(12) United States Patent
Viana et al.

(10) Patent No.: US 12,296,130 B2
(45) Date of Patent: May 13, 2025

(54) WEARABLE APPARATUS FOR PRODUCING VAPORS OF VOLATILE COMPOUNDS

(71) Applicants: Lidia Viana, Miami, FL (US); Aida Viana, Miami, FL (US)

(72) Inventors: Lidia Viana, Miami, FL (US); Aida Viana, Miami, FL (US)

( * ) Notice: Subject to any disclaimer, the term of this patent is extended or adjusted under 35 U.S.C. 154(b) by 1058 days.

(21) Appl. No.: 17/159,072

(22) Filed: Jan. 26, 2021

(65) Prior Publication Data

US 2021/0228834 A1 Jul. 29, 2021

Related U.S. Application Data

(60) Provisional application No. 62/966,013, filed on Jan. 26, 2020.

(51) Int. Cl.
*A61M 21/00* (2006.01)
*A61M 37/00* (2006.01)

(52) U.S. Cl.
CPC ..... *A61M 37/00* (2013.01); *A61M 2021/0016* (2013.01); *A61M 2209/088* (2013.01)

(58) Field of Classification Search
CPC ....... A61M 2021/0016; A61L 9/01–22; A61H 2201/102
See application file for complete search history.

(56) References Cited

U.S. PATENT DOCUMENTS

| | | | | |
|---|---|---|---|---|
| 2006/0251609 | A1* | 11/2006 | Sojka | B32B 27/36 424/76.1 |
| 2007/0183940 | A1* | 8/2007 | Yamamoto | A01M 1/2033 501/98.4 |
| 2009/0008411 | A1* | 1/2009 | Schumacher | A01M 1/2033 222/175 |
| 2012/0288414 | A1* | 11/2012 | Shi | A01M 1/2055 422/124 |
| 2015/0352241 | A1* | 12/2015 | Furner | A01M 1/2033 422/105 |
| 2021/0393005 | A1* | 12/2021 | Eun | A61L 9/03 |

FOREIGN PATENT DOCUMENTS

CN 107823688 A * 3/2018

* cited by examiner

*Primary Examiner* — Thaddeus B Cox
(74) *Attorney, Agent, or Firm* — Hubbard Law, PLLC

(57) ABSTRACT

A vapor delivery device comprises an enclosure having a fastener on a back side adapted for connecting to clothing and a front side with one or more openings, through which vapor of aroma compounds inside the enclosure may diffuse into the air for inhalation by a person wearing the device. The device includes a tray on which a substrate containing the aroma compound is held. The tray slides into and out of the enclosure through a pivoting or swinging motion.

11 Claims, 4 Drawing Sheets

WEARABLE APPARATUS FOR PRODUCING VAPORS OF VOLATILE COMPOUNDS

RELATED APPLICATION

This application claims the benefit of U.S. Provisional Application No. 62/966,013 filed Jan. 26, 2020, which is incorporated by reference herein for all purposes.

FIELD OF INVENTION

The invention pertains wearable apparatus for producing vapor of aromatics compounds for inhalation.

BACKGROUND

Aroma compounds have a smell or odor that can be sensed by a person's olfactory system, with a small enough molecular weight to be transported to the olfactory system in the nose. Aroma compounds are typically volatile, meaning that they will volatilize or easily evaporate at normal or room temperatures. Once the compounds evaporate to create vapors, the vapors will diffuse into the air and can be inhaled. It is thought that inhaling vapors produced from essential oils may have medicinal or other benefits.

SUMMARY

The invention pertains to apparatus and methods of delivering vapors of aroma compounds for inhalation.

In a representative embodiment, a device comprising an enclosure having a fastener on a back side adapted for connecting to clothing and a front side with one or more openings, through which vapor of aroma compounds inside the enclosure may diffuse into the air for inhalation by a person wearing the device. The device includes a tray on which a substrate containing the aroma compound is held. The tray slides into and out of the enclosure through a pivoting or swinging motion. A user swing the tray out from the enclosure to place the substrate on the tray and to swing it back so that the tray is contained within the enclosure along with the substrate, the tray positioning the substrate near the at least one opening.

The device allows placement of a source of vapors of aroma or other types of compounds on clothing discretely and in a location sufficiently close to allow vapors to be inhaled.

DETAILED DESCRIPTION OF EXEMPLARY EMBODIMENTS

In the following description, like numbers refer to like elements.

Figure 1:
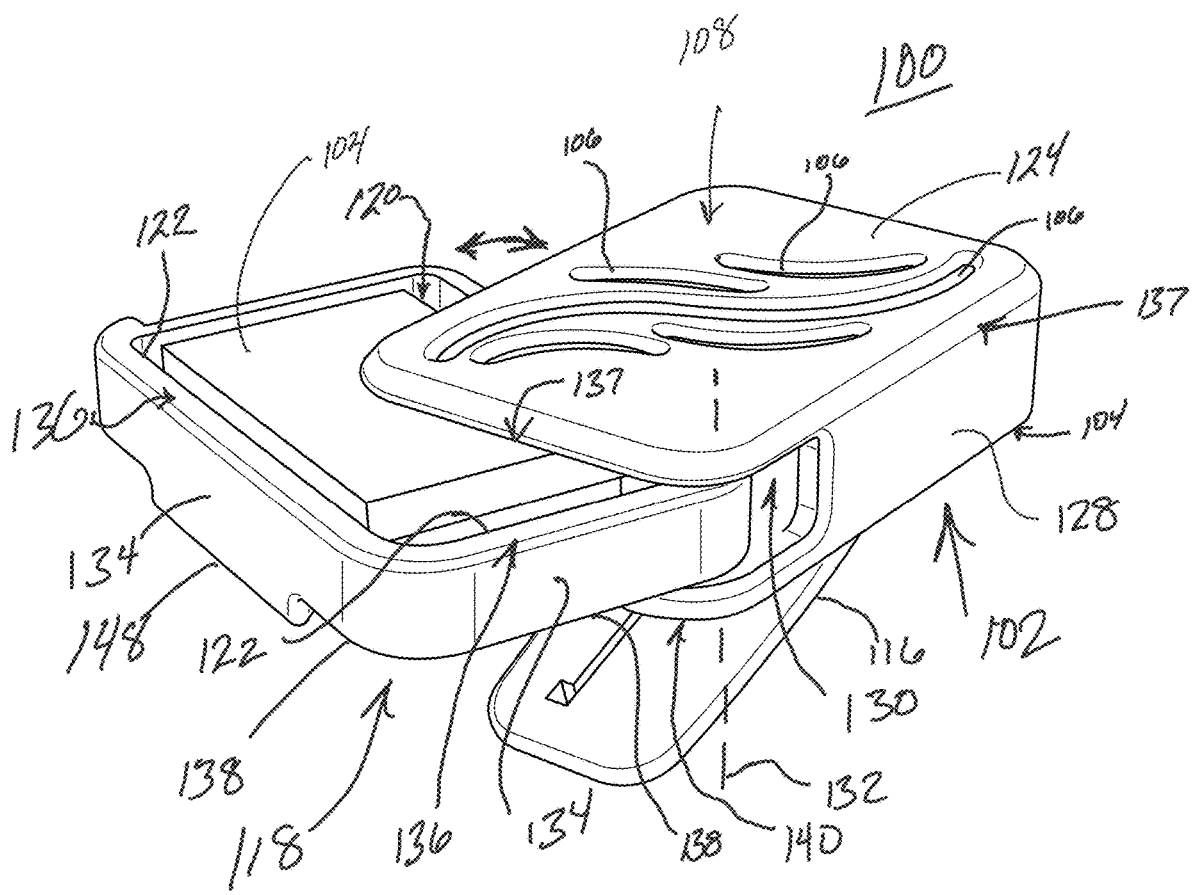
FIG. 1 is a perspective view of a device in an open position that can be fastened to clothing that holds a substrate containing compounds that evaporate and diffuse through openings in the device. vapors of those compounds in the vi
Figure 2:
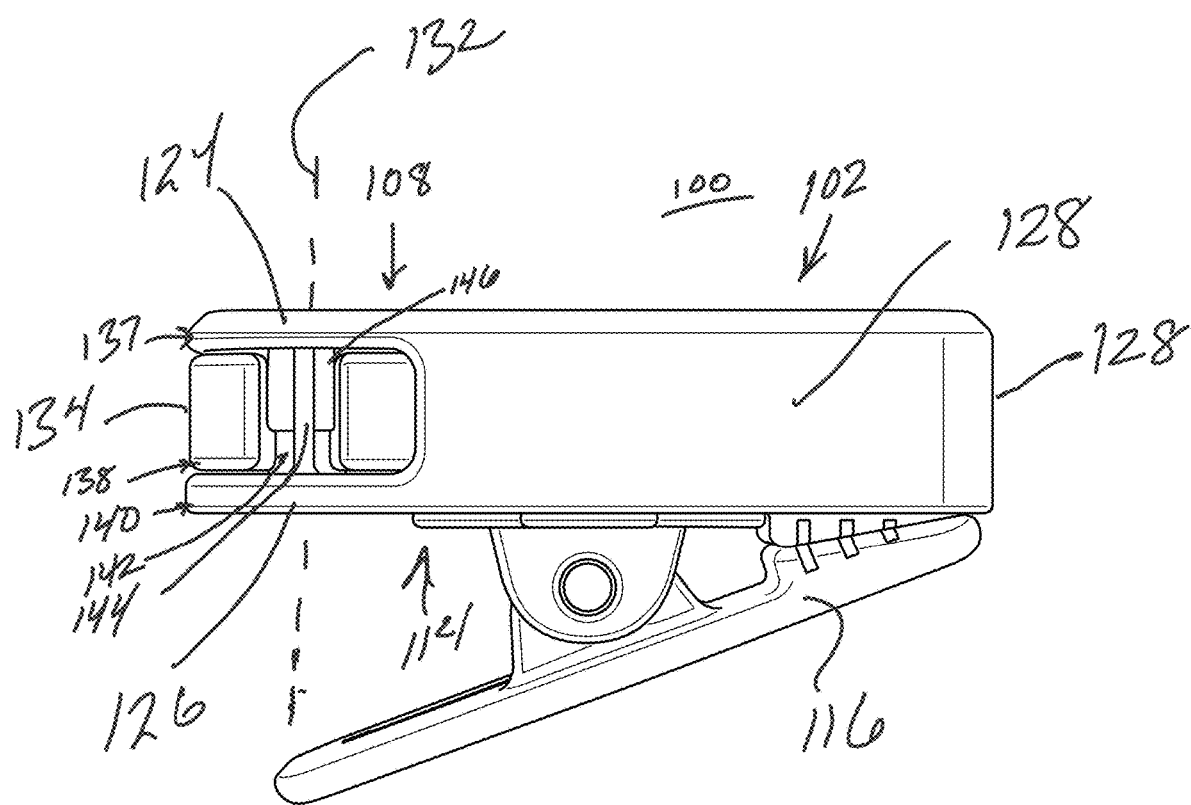
FIG. 2 is a side view of the device of FIG. 1 with the device in a closed position.
Figure 3:
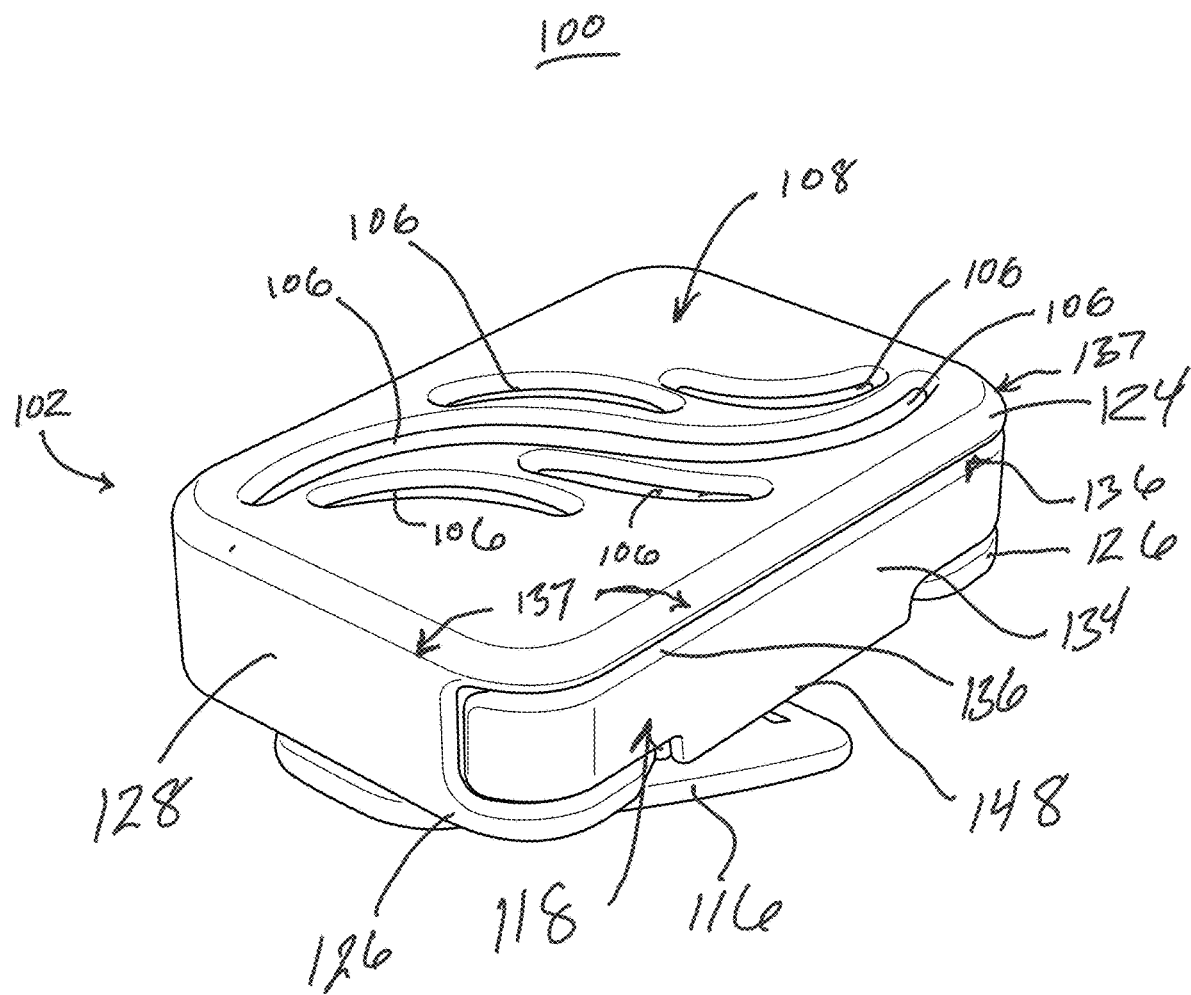
FIG. 3 is a top, side perspective view of the device of FIG. 2.
Figure 4:
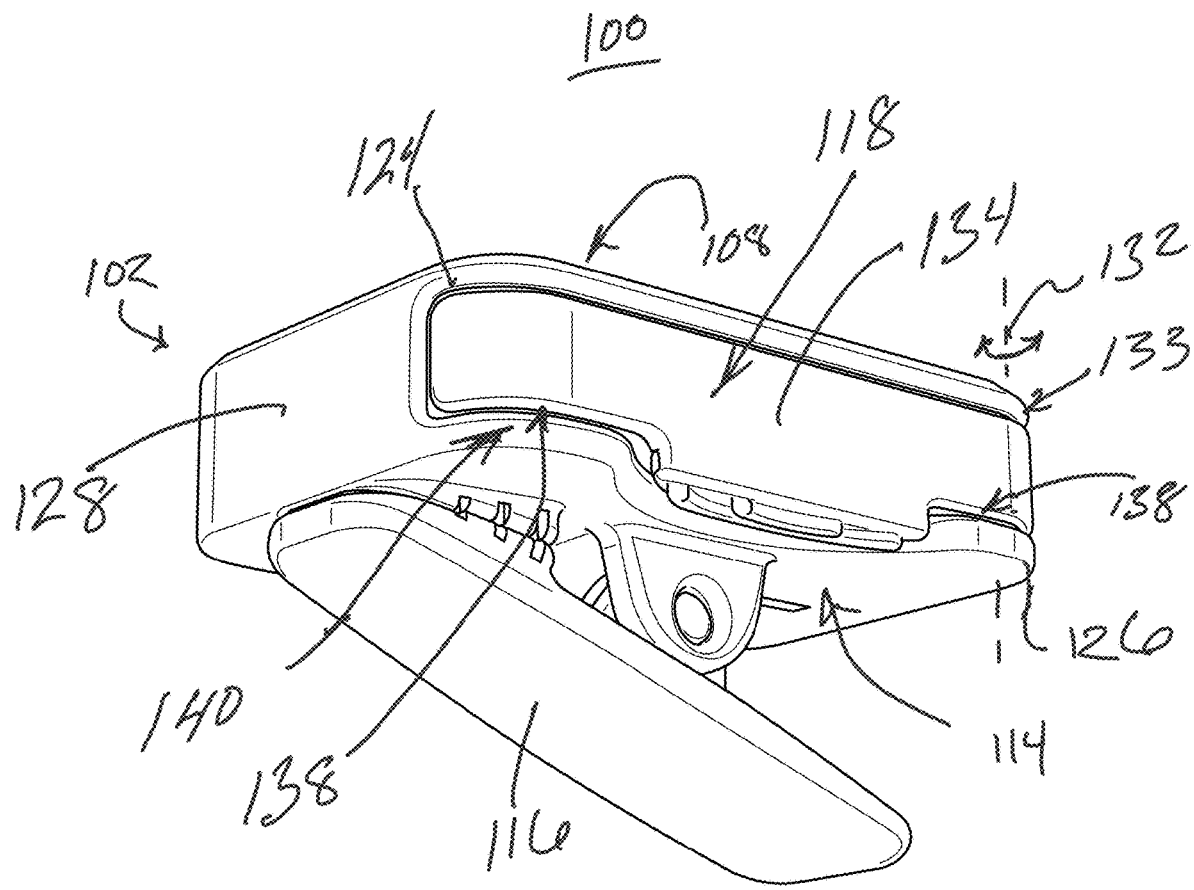
FIG. 4 bottom, side perspective view of the device of FIG. 2.

FIGS. 1 to 4 depicts an embodiment of a wearable device 100 that connects to a person's clothing and diffuses aroma compounds for inhalation by the person wearing the device. The embodiment is intended to be representative of devices that incorporate one or more of the features described below. The device 100 is comprised of an enclosure 102 that may be connected to clothing (not shown) at a location desired by the person wearing the device. It may further comprise a substrate 104 containing aroma compounds or other chemical compounds that will volatilize or evaporate at or around normal room temperatures, without the application of heat, and diffuse into the atmosphere outside the enclosure through a plurality of openings 106 defined in a front side 108 of the enclosure. The enclosure 102 retains the substrate 104. The substrate cannot fall out of or be removed from the enclosure when it is in a closed position, as shown in FIGS. 2-4, and must be opened as shown in FIG. 1.

In alternative embodiments, the front side may one or more openings. Each opening has a shape and size that prevents the substrate from falling through it.

The number and size of openings may be chosen or, optionally, made adjustable to increase or decrease the total area of the openings to increase or decrease the rate diffusion of vapor. In the illustrated embodiment, the openings relatively long and narrow, which provide a relatively large amount of open area while still retaining the substrate and restricting visual sight lines into the disclosure. However, in alternative embodiments, the openings may have a different shape, or multiple different shapes, and may have multiple different sizes. Furthermore, the openings may be partially or completely covered using louvered or mesh-like structure that vapors to escape but also retain the substrate within the disclosure and make it more difficult to see inside the disclosure. Furthermore, the shape, size, and arrangement of openings may be chosen to create decorative patterns that make the device more aesthetically pleasing. Although the illustrated embodiment does not have any, the enclosure may optionally have one or more openings located elsewhere in the enclosure, from which vapor may be diffused.

The enclosure in this embodiment has a relatively narrow thickness 108 (measured front to back) as compared to its length 110 and width 112. This gives it a relatively low profile when worn with its back surface 114 is placed next to the person's clothing.

Disposed on the back surface 114 is a fastener 116 that is capable of connecting the enclosure to clothing worn by a person and/or that is capable of connecting the enclosure to a fashion accessory worn by the person, such as a necklace. In this representative example the fastener comprises a clip capable of pinching a small amount of fabric to hold the enclosure on clothing, such as a shirt, blouse, dress or coat, allowing it to be placed in the vicinity of the wearer's nose. Optionally, the clip is capable of clasping a necklace or similar fashion accessory. Alternative, non-limiting examples of fasteners that may be suitable include hooks, buttons, pins, clasps, and similar fasteners that are capable of attaching the enclosure to clothing and/or fashion accessories.

The substrate functions to contain compounds to be evaporated to create the desired vapor for inhaling. The substrate is relatively thin as compared to its length and width, which allows it to have a large area for evaporation that faces openings 106 while permitting the enclosure 102 to be relatively. The substrate may be provided with the enclosure or provided separately. It may also be provided without the compounds to be evaporated, permitting a user to add the compounds to the substrate. Non-limiting example of the substrate 104 includes a pad that is comprised of a thin, relative to its length and width, piece of absorbent material. The pad may, optionally, be provided soaked or saturated with a liquid containing the compounds to be evaporated. Alternatively, the substrate can made of another type of solid material capable of holding the compounds to be evaporated. Non-limiting examples of liquids held by the pad or substrate include essential oils.

In one embodiment, the enclosure is provided with one or more substrates, such as pads. In another embodiment, the enclosure is provided with one or more replaceable substrates containing the compounds to be evaporated in a sealed package, non-limiting examples of which include pads containing with a liquid that includes compounds to be evaporated and pads soaked, impregnated, or saturated with essential oils.

A tray 118 with a receptacle 120 for holding the substrate 104 is received within the enclosure 102. The tray swings outwardly from the enclosure from a closed position shown in FIGS. 2-4 to an open position, one of which is shown in FIG. 1, that makes receptacle 120 accessible to insert a substrate into or remove (and optionally replace or change) a substrate from the enclosure 102, The tray comprises a rim 122 rising from a relatively flat bottom surface of the tray (not shown) and extending around the perimeter of the tray, thereby defining the receptacle 120 that holds the substrate 104. The receptacle holds the substrate when the enclosure is open and closed, thus making it relatively simple, easy and quick to place, change, or recharge a substrate 104. The receptacle 120 and substrate 104 may, optionally, have complementary shapes, like the one shown in FIG. 1, to reduce movement of the substrate within the enclosure. It is preferable, though not required, that the receptable have dimensions allows some room between it and the rim 122 for manually grasping the substrate to remove it.

The illustrated embodiment of enclosure 102 is comprised of a front wall 124, a a back wall 126 and a side wall 128 that joins front wall 124 and 126. The top, bottom and side walls at least partially define interior volume or chamber 130 in which tray 118 is received. When received, the tray cooperates with a bottom surface of the front wall 124 to trap the substrate 104. The top and back walls are flat and are spaced apart at the same distance. They could be said to be substantially planar and parallel to each other. They are also have substantially the same, rectangular shape and dimensions. The result is an enclosure and a chamber having box-like shapes. These characteristics offer certain advantages in terms of construction, assembly and closeness and ease of fit of the tray within chamber 130. However, in alternative embodiments, the top and back walls could be concave or convex and can differ in size and/or shape; they need not be parallel or spaced apart along their respective perimeters at a consistent distance. For example, each of the top and back walls could have triangular, polygonal, or other rectilinear shapes; circular, elliptical or other curved or arcuate shapes; a combination of straight and curved sides; or free-form.

The side wall 128 extends only partially around the perimeters of front wall 124 and back walls 126 to allow the tray 118 to be able to rotate or pivot about axis 132 between the closed position shown in FIGS. 2-4 and the open position shown in FIG. 1. The tray 118 is comprised of an outer side wall 134 that, when the tray is in a closed position, cooperates with at least the front wall 124 to prevent the substrate 104 from falling out of the device 100 when the tray is rotated to the closed position. Although not required, a top edge 136 of outer side wall 134 of the tray fits closely with a bottom surface (not visible) of the front wall 124. It also aligns with the outer perimeter edge 137 of the front wall 124, and a bottom, outer perimeter edge 138 of the tray aligns with an outer perimeter edge 140 of the back wall 126.

Rather translating linearly, the tray rotates or pivots about an axis 132 to allow the tray to be swung out of the enclosure 102 while remaining joined to it, though it still may be removed. The tray includes a pocket 142 that receives a post or pin 144, around which the tray rotates. The pocket is open, which allows the tray to be removably retained to the pin using, for example, spacer or bearing 146 or other means.

Room temperature is, in one embodiment, between 60 and 100 degrees and, in another embodiment, between 65 and 80 degrees.

The foregoing description is of exemplary and preferred embodiments. The invention, as defined by the appended claims, is not limited to the described embodiments. Alterations and modifications to the disclosed embodiments may be made without departing from the invention. The meaning of the terms used in this specification are, unless expressly stated otherwise, intended to have ordinary and customary meaning and are not intended to be limited to the details of the illustrated or described structures or embodiments.

What is claimed is:

1. An apparatus to be worn by a person for delivery of a vapor of one or more volatile aroma compounds, comprising:
   a substrate containing the one or more volatile aroma compounds that will evaporate at a room temperature between 60 and 100 degrees Fahrenheit;
   a tray on which the substrate can be placed;
   an enclosure for receiving the tray, the enclosure comprising:
      a front wall and a back wall separated by at least one side wall, wherein the front wall, the back wall, and the at least one side wall define between them a chamber in which the tray may fit;
      a fastener disposed on an exterior surface of the back wall, the fastener being adapted for removably connecting the enclosure to clothing; and
      at least one opening defined in the front wall;
   wherein the tray rotates about an axis to allow the person to swing the tray between an open position outside the chamber, where the substrate can be placed on the tray, and a closed position with the tray received inside the chamber, and wherein the substrate, when in the tray and when the tray is in the closed position, is trapped between the tray and the front wall adjacent the at least one opening, the vapor from the substrate diffusing outside the enclosure through the at least one opening.

2. The apparatus of claim 1, wherein the tray comprises a rim around its perimeter that defines a receptacle in which the substrate is placed; and wherein the tray has an exterior side wall that, when the tray is in the closed position, further defines the chamber in combination with the front wall, the back wall, and the at least one side wall.

3. The apparatus of claim 1, wherein the substrate comprises a pad soaked with a liquid containing the one or more volatile aroma compounds.

4. The apparatus of claim 1, wherein the fastener is comprised of a clip.

5. An apparatus for delivery of a vapor from one or more volatile aroma compounds that volatilize at at a room temperature between 65 and 80 degrees Fahrenheit, comprising:
   a tray defining a receptacle;

an enclosure, the enclosure comprising:
a front wall and a back wall separated by a side wall that extends at least partially around outer perimeters of the front and back walls;
a fastener disposed on an exterior surface of the back wall, the fastener being adapted for removably connecting the enclosure to clothing;
at least one opening defined in the front wall; and
wherein the tray rotates about an axis to allow a user to swing the tray between an open position in which the receptacle is accessible, and a closed position in which the receptacle and a top wall form a chamber adjacent the at least one opening, the chamber having a size and shape capable of retaining a thin substrate containing the one or more volatile aroma compounds while permitting the vapor of the one or more volatile compounds from the substrate to diffuse outside the enclosure through the at least one opening.

6. The apparatus of claim 5, wherein the tray comprises a rim around its perimeter that defines the receptacle; and wherein the tray has an exterior side wall that, when the tray is in the closed position, defines the chamber in combination with the front wall, the back wall, and the side wall.

7. The apparatus of claim 5, wherein the fastener is comprised of a clip.

8. A method for delivery of aroma vapors from one or more volatile aroma compounds comprising:
placing a substrate containing the one or more volatile aroma compounds on a tray;
inserting the tray in a chamber formed in part by an enclosure comprising a front wall and a back wall separated by at least one side wall, wherein the front wall, the back wall, and the at least one side wall define the chamber, and at least one opening defined in the front wall;
removably connecting the enclosure to an item of clothing or fashion accessory worn by a person with a fastener disposed on an exterior surface of the back wall;
wherein the tray rotates about an axis to allow the person to swing the tray between an open position outside the chamber and a closed position with the tray received inside the chamber, wherein the substrate is placed on the tray when the tray is in the open position; and
wherein the substrate, when in the tray and when the tray is in a closed position, is trapped between the tray and the front wall adjacent the least one opening, the aroma vapors from the substrate diffusing outside the enclosure through the at least one opening.

9. The method of claim 8, wherein the tray comprises a rim around its perimeter that defines a receptacle in which the substrate is placed; and wherein the tray has an exterior side wall that, when the tray is in the closed position, further defines the chamber in combination with the front wall, the back wall, and the at least one side wall.

10. The method of claim 8, wherein the substrate comprises a pad soaked with a liquid containing the one or more volatile aroma compounds.

11. The method of claim 8, wherein the substrate comprises a pad soaked with one or more essential oils.

* * * * *